United States Patent [19]

Ujiie et al.

[11] Patent Number: 5,294,718
[45] Date of Patent: Mar. 15, 1994

[54] PIPERIDINO-3,4-DIHYDROCARBOSTYRIL COMPOUNDS

[75] Inventors: Arao Ujiie; Hiromu Harada; Akira Iyobe; Masahiko Uchida; Koji Kamata, all of Nagano, Japan

[73] Assignee: Kissei Pharmaceutical Co., Ltd., Nagano, Japan

[21] Appl. No.: 101,006

[22] Filed: Aug. 3, 1993

[51] Int. Cl.$^5$ .................. C07D 401/10; A61K 31/47; A61K 31/445
[52] U.S. Cl. .................................. 546/158; 514/312; 514/314
[58] Field of Search .................. 546/158; 514/312, 314

[56] References Cited

U.S. PATENT DOCUMENTS

| | | | |
|---|---|---|---|
| 4,415,572 | 11/1983 | Tominaga | 546/158 |
| 4,435,404 | 3/1984 | Nishi | 546/157 |
| 4,454,130 | 6/1984 | Tominaga | 546/158 |
| 4,482,560 | 11/1984 | Banno | 546/158 |
| 4,487,772 | 12/1984 | Tominaga | 546/156 |
| 4,514,401 | 4/1985 | Tominaga | 514/253 |
| 4,593,035 | 6/1986 | Tominaga | 514/312 |
| 4,710,507 | 12/1987 | Campbell | 514/312 |
| 4,728,653 | 3/1988 | Campbell | 546/158 |
| 4,728,654 | 3/1988 | Campbell | 546/158 |
| 4,840,955 | 6/1989 | Sircar | 514/278 |
| 4,909,829 | 3/1990 | Theodoridis | 546/158 |
| 4,921,862 | 5/1990 | Walker | 546/158 |
| 5,071,856 | 12/1991 | Tamada | 514/312 |
| 5,166,160 | 11/1992 | Phillips | 514/312 |
| 5,212,181 | 5/1993 | Frost | 546/158 |

Primary Examiner—C. Warren Ivy
Assistant Examiner—Margaret M. Mach
Attorney, Agent, or Firm—Sughrue, Mion, Zinn, Macpeak & Seas

[57] ABSTRACT

Piperidino-3,4-dihydrocarbostyril compounds represented by the formula:

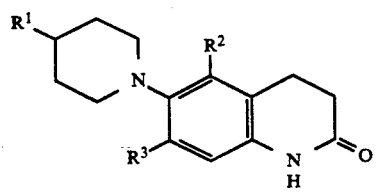

wherein $R^1$ represents a hydroxy group or an acyloxy group having 2 to 11 carbon atoms; one of $R^2$ and $R^3$ represents a nitro group, a cyano group, an alkoxycarbonyl group having 2 to 7 carbon atoms, an alkyl group having 1 to 4 carbon atoms, a haloalkyl group having 1 to 3 carbons atoms, or a halogen atom, and the other represents a hydrogen atom; and pharmaceutically acceptable salts thereof, exhibit platelet aggregation inhibiting activity and thus being useful as therapeutic agents for the prevention or treatment of cerebral ischemic disorders and arterial ischemic disorders.

5 Claims, No Drawings

PIPERIDINO-3,4-DIHYDROCARBOSTYRIL COMPOUNDS

FIELD OF THE INVENTION

The present invention relates to piperidino-3,4-dihydrocarbostyril compounds being useful for therapeutic agents.

More particularly, the present invention relates to novel piperidino-3,4-dihydrocarbostyril compounds represented by the formula:

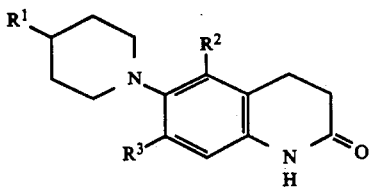

wherein $R^1$ represents a hydroxy group or an acyloxy group having 2 to 11 carbon atoms; one of $R^2$ and $R^3$ represents a nitro group, a cyano group, an alkoxycarbonyl group having 2 to 7 carbon atoms, an alkyl group having 1 to 4 carbon atoms, a haloalkyl group having 1 to 3 carbon atoms, or a halogen atom, and the other represents a hydrogen atom; and pharmaceutically acceptable salts thereof.

BACKGROUND OF THE INVENTION

Up to the present, as therapeutic agents for cerebral ischemic disorders and for arterial ischemic disorders, platelet aggregation inhibitors or antithrombotic agents such as ticlopidine, cilostazole and prostacyclines have been employed usually.

However, these agents often exhibit undesirable side effect such as headache, tachycardia, and hepatic disorders.

Therefore, more desirable therapeutic agents which exhibit more specific anti-platelet action with less undesirable side effect have been desired.

PRIOR ART

Japanese Patent Application (OPI) No.108688/90 (The term "OPI" used herein refers to an unexamined Japanese Patent Application) discloses that the carbostyril compound represented by the formula:

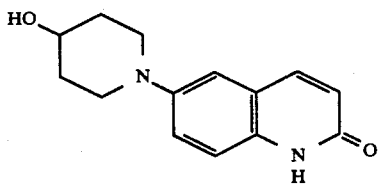

exhibits cardiac stimulating action, vasodilating action and hypotensive action, and is useful as cardiac stimulator, vasodilator and hypotensor.

SUMMARY OF THE INVENTION

An object of the present invention is to provide novel piperidino-3,4-dihydrocarbostyril compounds and pharmaceutically acceptable salts thereof which exhibit platelet aggregation inhibiting activity and thus are useful as an anti-platelet agent.

A further object of the present invention is to provide pharmaceutical compositions containing a piperidino-3,4-dihydrocarbostyril compound or a pharmaceutically acceptable salt thereof as an active ingredient.

Other object, features and advantages of the present invention will be apparent from the following description of the invention.

DETAILED DESCRIPTION OF THE INVENTION

The present invention provides piperidino-3,4-dihydrocarbostyril compounds and pharmaceutically acceptable salts thereof which exhibit platelet aggregation inhibiting activity.

Thus, the piperidino-3,4-dihydrocarbostyril compounds and pharmaceutically acceptable salts thereof of the present invention are useful as therapeutic agents for the prevention or treatment of cerebral ischemic disorders and arterial ischemic disorders.

The term "acyloxy group" used in the present invention means an aliphatic or aromatic acyloxy group having 2 to 11 carbon atoms, for example, acetoxy, propionyloxy, benzoyloxy or naphthoyloxy group are included.

The term "alkoxycarbonyl group" used in the present invention means a straight or branched alkyloxycarbonyl group having 2 to 7 carbon atoms, for example, methoxycarbonyl, ethoxycarbonyl, isopropoxycarbonyl or tertiarybutoxycarbonyl group are included.

The term "alkyl group" used in the present invention means a straight or branched alkyl group having 1 to 4 carbon atoms, for example, methyl, ethyl, isopropyl or tertiarybutyl group are included.

The term "haloalkyl group" used in the present invention means a straight or branched alkyl group having 1 to 3 carbon atoms and substituted with one or more halogen atoms, for example, chloromethyl, trifluoromethyl or trichloroethyl group are included.

The term "halogen atom" used in the present invention means a fluorine atom, a chlorine atom or a bromine atom.

Of the piperidino-3,4-dihydrocarbostyril compounds represented by the formula (I) of the present invention, a compound represented by the formula:

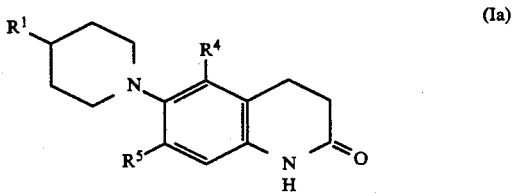

wherein $R^1$ has the same meaning as described above; one of $R^4$ and $R^5$ represents a fluorine atom, an alkyl group having 1 to 4 carbon atoms or a haloalkyl group having 1 to 3 carbon atoms and the other represents a hydrogen atom, can be prepared by a catalytic hydrogenating cyclization from an o-nitrocinnamic acid compound represented by the formula:

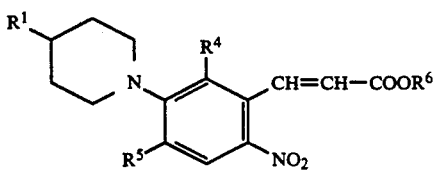
(III)

wherein $R^1$, $R^4$ and $R^5$ have the same meanings as described above; $R^6$ represents a hydrogen atom or an alkyl group having 1 to 4 carbon atoms, using a catalyst such as palladium on carbon, platinum oxide or Raney nickel in an inert solvent such as methanol, ethanol, acetic acid or tetrahydrofuran, and then in case of a compound wherein $R^1$ represents a hydroxy group, if desired, the resulting compound is acylated with a carboxylic acid represented by the formula:

R'OH    (IV)

wherein R' represents an aromatic acyl group or an aliphatic acyl group, or with a reactive functional derivative thereof.

Of the piperidino-3,4-dihydrocarbostyril compounds represented by the formula (I) of the present invention, a compound represented by the formula:

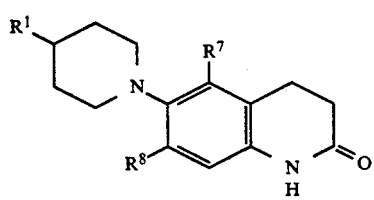
(Ib)

wherein $R^1$ has the same meaning as described above; one of $R^7$ and $R^8$ represents a nitro group, and the other represents a hydrogen atom, can be prepared by a catalytic hydrogenating cyclization from an o-nitrocinnamic acid compound represented by the formula:

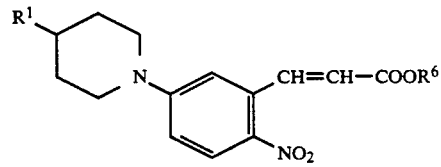
(V)

wherein $R^1$ and $R^6$ have the same meanings as described above, and then nitration of the resulting piperidino-3,4-dihydrocarbostyril compound represented by the formula:

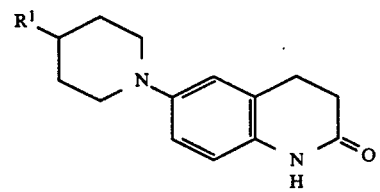
(VI)

wherein $R^1$ has the same meaning as described above, using a nitrating agent such as fuming nitric acid, concentrated nitric acid, sodium nitrite, potassium nitrite, sodium nitrate or potassium nitrate in the presence or absence of a solvent such as acetic acid, trifluoroacetic acid, hydrochloric acid or sulfuric acid, and then, in case of a compound wherein $R^1$ represents a hydroxy group, if desired, the resulting compound is acylated in the same manner as described above.

Of the piperidino-3,4-dihydrocarbostyril compounds represented by the formula (I) of the present invention, a compound represented by the formula:

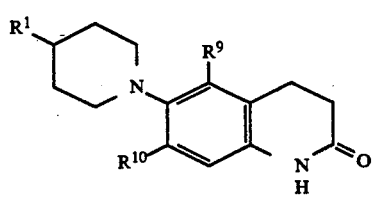
(Ic)

wherein $R^1$ has the same meaning as described above; one of $R^9$ and $R^{10}$ represents a chlorine atom or a bromine atom, and the other represents a hydrogen atom, can be prepared by halogenating the piperidino-3,4-dihydrocarbostyril compound represented by the formula (VI) using a halogenating agent such as N-bromosuccinimide (NBS), N-chlorosuccinimide (NCS), bromine or chlorine in the presence or absence of an inert solvent such as chloroform, methylene chloride, carbon tetrachloride, benzene or acetic acid, and then, in case of a compound where $R^1$ represents a hydroxy group, if desired, the resulting compound is acylated in the same manner as that described above.

Of the piperidino-3,4-dihydrocarbostyril compounds represented by the formula (I) of the present invention, a compound represented by the formula:

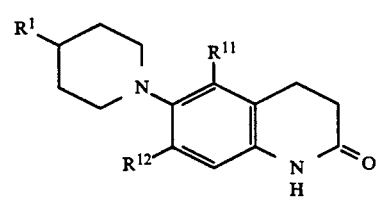
(Id)

wherein $R^1$ has the same meaning as described above; one of $R^{11}$ and $R^{12}$ represents a cyano group, and the other represents a hydrogen atom, can be prepared by reacting the piperidino-3,4-dihydrocarbostyril compound represented by the formula (Ic) with a cyanide compound represented by the formula:

$R^{13}CN$    (VII)

wherein $R^{13}$ represents a copper, a sodium or a potassium, in an inert solvent such as N,N-dimethylformamide, dimethylsulfoxide, ethanol or pyridine.

Furthermore, of the piperidino-3,4-dihydrocarbostyril compounds represented by the formula (I) of the present invention, a compound represented by the formula:

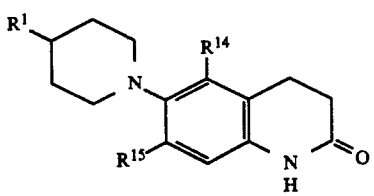

(Ie)

wherein $R^1$ has the same meaning as described above; one of $R^{14}$ and $R^{15}$ represents a lower alkoxycarbonyl group, and the other represents a hydrogen atom, can be prepared by saponifying the piperidino-3,4-dihydrocarbostyril compound represented by the formula (Id) under an alkaline condition such as sodium hydroxide solution, and then esterifying the resulting carboxylic acid compound using diazomethane or an alcohol in a usual manner, and then, in case of a compound where $R^1$ represents a hydroxy group, if desired, the resulting compound is acylated in the same manner as that described above.

o-Nitro cinnamic acid compounds of the formulae (III) and (V) used as starting materials in the present invention, are novel compounds and can be prepared as follows. That is, an acetal compound represented by the formula:

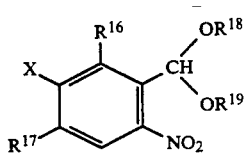

(VIII)

wherein X represents a chlorine atom or a bromine atom; one of $R^{16}$ and $R^{17}$ represents a hydrogen atom, a lower alkyl group or a fluorine atom, and the other represents a hydrogen atom; $R^{18}$ and $R^{19}$ represent a lower alkyl group or combines each other to form an alkylene chain, is reacted with 4-piperidinol in the presence of a basic substance such as triethylamine, pyridine, 1,6-diazabicyclo[5,4,0]-7-undecene or 1,5-diazabicyclo[4,3,0]-5-nonene, or with an excess amount of 4-piperidinol in an inert solvent to give a piperidinobenzene compound represented by the formula:

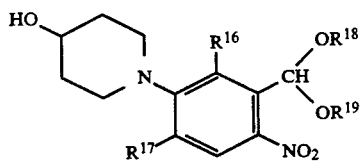

(IX)

wherein $R^{16}$, $R^{17}$, $R^{18}$ and $R^{19}$ have the same meanings as described above, and then, the obtained compound of the formula (IX) is treated with a mineral acid such as hydrochloric acid or sulfuric acid in an aqueous alcohol or an aqueous acetone to remove the protective group, and followed by the dehydrating condensation reaction of the resulting compound with a malonic acid compound represented by the formula:

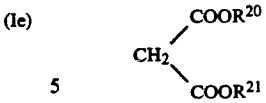

(X)

wherein $R^{20}$ represents a hydrogen atom or an alkyl group; $R^{21}$ represents a hydrogen atom or an alkali metal, in the presence of a basic substance such as piperidine, triethylamine, pyridine, 1,8-diazabicyclo[5,4,0]-7-undecene or 1,5-diazabicyclo[4,3,0]-5-nonene in an inert solvent to give the above o nitro cinnamic acid compound.

The acetal compound of formula (VIII) using as a starting material in the above process can be prepared as follows. That is, a benzaldehyde compound represented by the formula:

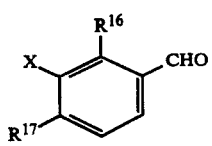

(XI)

wherein X, $R^{16}$ and $R^{17}$ have the same meanings as described above, is nitrated with a nitrating agent in the presence or absence of the solvent to give a nitro compound represented by the formula:

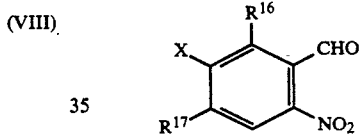

(XII)

wherein X, $R^{16}$ and $R^{17}$ have the same meanings as described above, and the nitrated compound of the formula (XII) is treated with a protecting reagent of a formyl group such as methanol, ethanol, ethyleneglycol or triethyl ortho formate to give the acetal compound of the formula (VIII).

The compounds of the formulae (IV), (VII) and (XI) used as other starting materials in the present invention, can be commercially available or can be easily prepared by a similar method to that disclosed in the literature.

Of the compounds represented by the formula (I) of the present invention, compounds wherein $R^1$ represents a hydroxy group are preferable, for example, 6-(4-hydroxypiperidino)-7 nitro-3,4-dihydrocarbostyril, 6-(4-hydroxypiperidino)-5-nitro-3,4-dihydrocarbostyril, 7-bromo-6-(4-hydroxypiperidino)-3,4-dihydrocarbostyril, 5-bromo-6-(4-hydroxypiperidino) 3,4-dihydrocarbostyril, 7-chloro-6-(4-hydroxypiperidino) 3,4-dihydrocarbostyril, 5-chloro-6-(4-hydroxypiperidino)-3,4-dihydrocarbostyril, 7-cyano-6-(4-hydroxypiperidino)-3,4-dihydrocarbostyril, 6-(4-hydroxypiperidino)-7-methoxycarbonyl-3,4-dihydrocarbostyril, 6-(4-hydroxypiperidino) 7-methyl-3,4-dihydrocarbostyril, 7-fluoro-6-(4-hydroxypiperidino)-3,4-dihydrocarbostyril and 6 (4-hydroxypiperidino)-7-trifluoromethyl-3,4-dihydrocarbostiril can be illustrated. Furthermore, 7-substituted compounds are more preferable than 5-substituted compounds, for example, 6-(4-hydroxypiperidino)-7-nitro 3,4-dihydrocarbostyril, 6-(4-hydroxypiperidino)-5 nitro-3,4-dihydrocarbostyril, 7-bromo-6-(4-hydroxypiperidino)-3,4-dihydrocarbostyril, 7-chloro-6-(4-hydroxypiperidino) 3,4-dihydrocarbostyril, 7-cyano-6-(4-hydroxypiperidino)-3,4-dihydrocarbostyril, 6-(4-hydroxypiperidino)-7-methoxycarbonyl-3,4-dihydrocarbostyril, 7-fluoro-6-(4-hydroxypiperidino)-3,4-dihydrocarbostyril and 6-(4-hydroxypiperidino)-7-trifluoromethyl-3,4-dihydrocarbostyril can be illustrated, and the most preferred compounds are 7-bromo 6-(4-hydroxypiperidino) 3,4-dihydrocarbostyril, 7-chloro-6 -(4-hydroxypiperidino)-3,4-dihydrocarbostyril, 7-cyano-6-(4-hydroxypiperidino)-3,4-dihydrocarbostyril, 7-fluoro 6-(4-hydroxypiperidino)-3,4-dihydrocarbostyril and 6-(4-hydroxypiperidino)-7-trifluoromethyl-3,4-dihydrocarbostyril.

The piperidino-3,4-dihydrocarbostyril compounds of the formula (I) of the present invention can be converted into pharmaceutically acceptable salts thereof according to conventional methods. Examples of such pharmaceutically acceptable salts include acid addition salts with an inorganic acid or an organic acid such as hydrochloric acid, hydrobromic acid, sulfuric acid, methanesulfonic acid, benzenesulfonic acid, p-toluenesulfonic acid, acetic acid, citric acid, succinic acid, tartaric acid and fumaric acid. These pharmaceutically acceptable salts possess the same platelet aggregation inhibiting activity, and thus being useful as anti-platelet agent.

When the piperidino-3,4-dihydrocarbostyril compounds of the formula (I) of the present invention or the pharmaceutically acceptable salts thereof are employed therapeutically, they can be administered in various dosage forms depending upon intended therapies. Administration of the compound for such therapeutic purpose may be oral or parenteral, using appropriate dosage forms, e.g. tablets, pills, powders, granules, capsules and injectable preparations. These pharmaceutical compositions can be formulated in accordance with a conventional method.

In molding the pharmaceutical compositions into a tablet form, a wide variety of conventional carriers known in the art can be used. Examples of suitable carriers are excipients such as glucose, lactose, sucrose, partly pregelatinized starch, micro-crystalline cellulose and calcium hydrogenphosphate, binders such as hydroxypropylcellulose, polyvinylpyrrolidone and croscarmellose sodium, disintegrators such as carmellose calcium and low substituted hydroxypropylcellulose, and lubricants such as magnesium stearate, calcium stearate and talc. The tablets, if desired, can be coated and made into sugar-coated tablets, gelatin-coated tablets, enteric-coated tablets, film-coated tablets, or tablets coated with two or more layers.

When the pharmaceutical composition is formulated into an injectable preparation, the resulting solution and suspension are preferably sterilized, and are isotonic with respect to blood. In formulating the pharmaceutical composition into the form of a solution and suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent in an amount sufficient to prepare and isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the piperidino-3,4-dihydrocarbostyril compounds of the present invention may be in a range from about 10 to 1000 mg per adult human by oral administration per day, or from about 1 to 100 mg per adult human by parenteral administration per day in multiple dose depending upon the type of diseases, the severity of condition to be treated, and like.

The present invention is further illustrated in more detail by way of the following Reference Examples, Examples and Test Example. The melting points of the products obtained are uncorrected.

REFERENCE EXAMPLE 1

5-(4-Hydroxypiperidino)-2-nitrobenzaldehyde dimethylacetal

A solution of 5 g of 5-chloro-2-nitrobenzaldehyde dimethylacetal and 8.8 g of 4-hydroxypiperidine in 20 ml of N,N-dimethylformamide was heated at 80° C. for 14 hr. The reaction mixture was poured into water, and extracted with ethyl acetate. The extract was washed with water, dried, and evaporated under a reduced pressure. The residue was purified by a silica gel column chromatography to give 4.3 g of 5-(4-hydroxypiperidino)-2-nitrobenzaldehyde dimethylacetal.

yellow oil

NMR (CDCl$_3$, 400 MHz)

δ: 1.60–1.69(2H, m), 1.96–2.02(2H, m), 3.19–3.25(2H, m), 3.47(6H, s), 3.76-3.82(2H, m), 3.96-3.99(1H, m), 6.07(1H, s), 6.78(1H, dd, J=9.2 Hz, J=2.9 Hz), 7.21(1H, d, J=2.9 Hz), 8.01(1H, d, J=9.2 Hz)

REFERENCE EXAMPLE 2

5-(4-Hydroxypiperidino)-2-nitro p-tolaldehyde dimethylacetal 5-(4-Hydroxypiperidino)-2-nitro-p-tolaldehyde dimethylacetal was prepared from 5-chloro-2-nitro-p-tolaldehyde dimethylacetal using the same procedure as that described as that described in Reference Example 1.

yellow oil

NMR (CDCl$_3$, 400 MHz)

δ: 1.48(1H, d, J=4.2 Hz), 1.70–1.80(2H, m), 2.00–2.10(2H, m), 2.33(3H, s), 2.80–2.90(2H, m), 3.20–3.30(2H, m), 3.43(6H, s), 3.85–3.95(1H, m), 5.97(1H, s), 6.78(1H, dd, J=9.2 Hz, J=2.9 Hz), 7.33(1H, s)

REFERENCE EXAMPLE 3

4-Fluoro-5-(4-hydroxypiperidino)-2-nitrobenzaldehyde dimethylacetal

4-Fluoro-5-(4-hydroxypiperidino)-2-nitrobenzaldehyde dimethylacetal was prepared from 4,5-difluoro-2-nitrobenzaldehyde dimethylacetal using the same procedure as that described in Reference Example 1.

yellow oil

NMR (CDCl$_3$, 400 MHz)

δ: 1.65–80(2H, m), 1.95–2.10(2H, m), 3.00–3.15(2H, m), 3.45(6H, s), 3.55–3.70(2H, m), 3.85–4.00(1H, m), 6.00(1H, s), 7.28(1H, d, J=10.4 Hz), 7.77(1H, d, J=12.6 Hz)

REFERENCE EXAMPLE 4

5-(4-Hydroxypiperidino)-2-nitrobenzaldehyde

To a solution of 4.3 g of 5-(4-hydroxypiperidino)-2-nitrobenzaldehyde dimethylacetal in 40 ml of acetone was added 40 ml of 2N hydrochloric acid. After refluxing for 15 min, the reaction mixture was poured into water, and extracted with ethyl acetate. The extract was washed with water, dried, and evaporated under a reduced pressure to give 3.5 g of 5-(4-hydroxypiperidino)-2-nitrobenzaldehyde.

orange-colored powder
NMR (CDCl₃, 400 MHz)
δ: 1.63–1.71(2H, m), 1.97–2.04(2H, m), 3.29–3.36(2H, m), 3.79–3.85(2H, m), 4.01–4.06(1H, m), 6.95(1H, dd, J=9.3 Hz, J=3.0 Hz), 7.14(1H, d, J=3.0 Hz), 8.10(1H, d, J=9.3 Hz), 10.53(1H, s)
mp 131°–133° C.

REFERENCE EXAMPLE 5

Ethyl 5-(4-hydroxypiperidino)-2-nitrocinnamate

To a solution of 10.1 g of 5 (4-hydroxypiperidino)-2-nitrobenzaldehyde and 34.4 g of ethyl malonate sodium salt in 120 ml of pyridine were added 9.9 g of concentrated sulfuric acid and 850 mg of piperidine. After refluxing for 1 hr, the reaction mixture was concentrated under a reduced pressure. Dilute hydrochloric acid was added to the residue and it was extracted with chloroform. The extract was washed with water, dried, and evaporated under a reduced pressure. The residue was purified by a silica gel column chromatography to give 10.6 g of ethyl 5-(4-hydroxypiperidino)-2-nitrocinnamate.

orange-colored oil
NMR (CDCl₃, 400 MHz)
δ: 1.35(3H, t, J=7.1 Hz), 1.63–1.71(2H, m), 1.98–2.03(2H, m), 3.23–3.29(2H, m), 3.75–3.81(2H, m), 3.99–4.04(1H, m), 4.29(2H, q, J=7.1 Hz), 6.22(1H, d, J=15.7 Hz), 6.80–6.86(2H, m), 8.10(1H, d, J=9.3 Hz), 8.29(1H, d, J=15.7 Hz)

REFERENCE EXAMPLE 6

6-(4-Hydroxypiperidino)-3,4-dihydrocarbostyril

A suspension of 5.2 g of ethyl 5-(4-hydroxypiperidino)-2-nitrocinnamate and 1 g of 5% palladium on carbon in 50 ml of acetic acid was stirred under a hydrogen atmosphere at 50° C. for 14 hr. The catalyst was filtrated off and the filtrate was concentrated under a reduced pressure. The resulting residue was purified by a silica gel column chromatography and recrystallized from ethanol to give 1.9 g of 6-(4-hydroxypiperidino)-3,4-dihydrocarbostyril.

colorless needles
NMR (DMSO-d₆, 400 MHz)
δ: 1.35–1.65(2H, m), 1.70–1.85(2H, m), 2.35–2.40(2H t, J=7.2 Hz), 2.65–2.85(4H, m), 3.30–3.45(2H, m), 3.50–3.65(1H, m), 4.64(1H, d, J=3.8 Hz), 6.65–6.77(3H, m), 9.81(1H, s)
mp 204°–211° C.

REFERENCE EXAMPLE 7

6-(4-Acetoxypiperidino)-3,4-dihydrocarbostyril

To a solution of 200 mg of 6-(4-hydroxypiperidino)-3,4-dihydrocarbostyril in 2 ml of pyridine were added 92 mg of acetic anhydride and 10 mg of 4-dimethylaminopyridine. After stirring at room temperature for 40 hr, the reaction mixture was concentrated under a reduced pressure, and the resulting residue was purified by a silica gel column chromatography to give 226 mg of 6-(4-acetoxypiperidino)-3,4-dihydrocarbostyril.

colorless needles
NMR (DMSO-d₆, 400 MHz)
δ: 1.61–1.69(2H, m), 1.85–1.95(2H, m), 2.01(3H, s), 2.36–2.40(2H, m), 2.79–2.92(4H, m), 3.29–3.38(2H, m), 4.76–4.80(1H, m), 6.70–6.78(2H, m), 6.80(1H, s), 9.82(1H, s)
mp 217°–222° C.

REFERENCE EXAMPLE 8

Ethyl 3-chloro-4-trifluoromethylcinnamate

A suspension of 3.5 g of 2,4-dichlorobenzotrifluoride, 1.28 g of triphenylphosphine, 865 mg of paradium(II) chloride, 2.68 g of sodium iodide, 712 mg of nickel(II) bromide, 4.94 g of triethylamine, and 1.79 g of ethyl acrylate in 16 ml of N,N-dimethylformamide was heated at 140° C. for over night in a sealed tube. The reaction mixture was filtrated off, and the filtrate was concentrated under a reduced pressure. The residue was extracted with ethyl acetate, the extract was washed with water, dried, and evaporated under a reduced pressure. The resulting residue was purified by a silica gel column chromatography to give 1.12 g of ethyl 3-chloro-4-trifluoromethylcinnamate.

pale brown crystal
NMR (CDCl₃, 400 MHz)
δ: 1.35(3H, t, J=7.1 Hz), 4.29(2H, q, J=7.1 Hz), 6.51(1H, d, J=16.0 Hz), 7.47–7.72(4H, m)
mp 65°–67° C.

REFERENCE EXAMPLE 9

Ethyl 5-chloro-2-nitro-4-trifluoromethylcinnamate

To a solution of 100 mg of ethyl 3-chloro-4-trifluoromethylcinnamate and 1.8 ml of concentrated sulfuric acid was added 42 ml of 60% nitric acid at −15° C. After stirring at the same temperature for a few minutes, the reaction mixture was poured into a cold water, and extracted with ethyl acetate. The extract was washed with water, dried, and evaporated. The residue was purified by a silica gel column chromatography to give 102 mg of ethyl 5-chloro-2-nitro-4-trifluoromethylcinnamate.

pale yellow crystals
NMR (CDCl₃, 400 MHz)
δ: 1.36(3H, t, J=7.1 Hz), 4.31(2H, q, J=7.1 Hz), 6.43(1H, d, J=15.9 Hz), 7.77(1H, s), 8.09(1H, d, J=15.8 Hz), 8.43(1H, s)
mp 42°–44° C.

REFERENCE EXAMPLE 10

Ethyl 5-(4-hydroxypiperidino)-2 nitro-4-trifluoromethvlcinnamate

A solution of 50 mg of ethyl 5-chloro-2 nitro-4-trifluoromethylcinnamate and 150 mg of 4-hydroxypiperidine in 2 ml of N,N-dimethylformamide was heated at 130° C. for 20 min. The reaction mixture was concentrated under a reduced pressure, and then 0.5N hydrochloric acid and ethyl acetate were added to the residue. The organic layer was washed with water, dried, and evaporated under a reduced pressure. The residue was purified by a silica gel column chromatography to give 20 mg of ethyl 5-(4-hydroxpiperidino)- 2-nitro-4-trifluoromethylcinnamate.

yellow viscous oil
NMR (CDCl₃, 400 MHz)
δ: 1.36(3H, t ,J=7.1 Hz), 1.73 1.81(2H ,m), 2.02–2.07(2H, m), 2.98–3.04(2H, m), 3.35–3.40(2H, m), 3.94–3.98(1H, m), 4.31(2H, q, J=7.1 Hz), 6.31(1H, d, J=15.8 Hz), 7.24(1H, s), 8.18(1H, d, J=15.8 Hz), 8.41(1H, s)

EXAMPLE 1

6-(4-Hydroxypiperidino)-7-nitro-3.4-dihydrocarbostyril (Compound 1)

6-(4-Hydroxypiperidino)-5-nitro-3.4-dihydrocarbostyril Compound 2)

To a solution of 3.1 g of 6-(4-hydroxypiperidino)-3,4-dihydrocarbostyril in 60 ml of acetic acid was added 1.7 g of sodium nitrite. After stirring at room temperature for 1 hr, water and a 17% methanol-chloroform mixture was added to the reaction mixture. The organic layer was washed with water, dried, and evaporated under a reduced pressure. The crude mixture was purified by a silica gel column chromatography and recrystallized from 2-propanol to give 1.1 g of 6-(4-hydroxypiperidino) 7-nitro-3,4-dihydrocarbostyril and 130 mg of 6-(4-hydroxypiperidino)-5-nitro-3,4 dihydrocarbostyril.

6-(4-Hydroxypiperidino)-7-nitro-3,4-dihydrocarbostyril (Compound 1)

red powder
NMR (DMSO-$d_6$, 400 MHz)
δ: 1.26–1.54 (2H, m), 1.79–1.82(2H, m), 2.44–2.56(2H, m), 2.73–2.79(2H, m), 2.94(2H, t, J=7.5 Hz), 3.03–3.08(2H, m), 3.57–3.64(1H, m), 4.67(1H, d, J=4 3 Hz), 7.23(1H, s), 7.30(1H, s), 10.16(1H, s)
mp 203°–206° C.

6-(4-Hydroxypiperidino)-5-nitro-3,4-dihydrocarbostyril (Compound 2)

orange-colored powder
NMR (DMSO-$d_6$, 270 MHz)
δ: 1.37–1.46(2H, m), 1.70–1.80(2H, m), 2.45–2.49(2H, m), 2.65–2.73(4H, m), 2.91–2.95(2H, m), 3.53–3.58(1H, m), 4.64(1H, d, J=4.4 Hz), 6.99(1H, d, J=8.7 Hz), 7.31(1H, d, J=8.7 Hz), 10.36(1H, s)
mp 258°–261° C.

EXAMPLE 2

7-Bromo-6-(4-hydroxypiperidino)-3,4-dihydrocarbostyril (Compound 3)

5-Bromo-6-(4-hydroxypiperidino)-3,4-dihydrocarbostyril (Compound 4)

To a solution of 300 mg of 6-(4-acetoxypiperidino)-3,4-dihydrocarbostyril in 7 ml of chloroform was added 370 mg of N-bromosuccinimide, and the mixture was stirred at room temperature for 1 hr. Then, an aqueous sodium thiosulfate was added to the reaction mixture, and the mixture was extracted with chloroform. The extract was washed with brine, dried and evaporated under a reduced pressure. The crude mixture was purified by a silica gel column chromatography to give 87 mg of 6-(4-acetoxypiperidino)-7-bromo-3,4-dihydrocarbostyril and 41 mg of 6-(4-acetoxypiperidino)-5-bromo-3,4-dihydrocarbostyril.

This 7-bromocarbostyril was dissolved in 2.5 ml of hydrogen chloride-methanol solution, and mixture was refluxed for 1 hr. The reaction mixture was concentrated and purified by a silica gel column chromatography to give 56 mg of 7-bromo-6-(4-hydroxypiperidino)-3,4-dihydrocarbostyril.

7-Bromo-6-(4-hydroxypiperidino)-3,4-dihydrocarbostyril (Compound 3)

white powder
NMR (DMSO-$d_6$, 270 MHz)
δ: 1.50–1.65(2H, m), 1.75–1.95(2H, m), 2.39–2.45(2H, m), 2.65–2.85(4H, m), 3.00–3.20(2H, m), 3.50–3.70(1H, m), 7.07(2H, s), 10.05(1H, s)
mp 209°–212° C.

The above 5-bromocarbostyril was dissolved in 1 ml of hydrogen chloride-methanol solution, and mixture was refluxed for 1 hr. The reaction mixture was concentrated and purified by a silica gel column chromatography to give 24 mg of 5-bromo-6-(4-hydroxypiperidino)-3,4-dihydrocarbostyril.

5-Bromo-6-(4-hydroxypiperidino)-3,4-dihydrocarbostyril (Compound 4)

white powder
NMR (DMSO-$d_6$, 400 MHz)
δ: 1.50–1.65(2H, m), 1.80–1.90(2H, m), 2.40–2.50(2H, m), 2.60–2.75(2H, m), 2 95–3.15(4H, m), 3.55–3.70(1H, m), 6.83(1H, d, J=8.0 Hz), 7.03(1H, d, J=8.0 Hz), 10.10(1H, s)
m 223°–226° C.

EXAMPLE 3

7-Chloro-6-(4-hydroxypiperidino)-3,4-dihydrocarbostyril (Compound 5)

5-Chloro-6-(4-hydroxypiperidino)-3,4-dihydrocarbostyril (Compound 6)

7-Chloro-6-(4-hydroxypiperidino)-3,4-dihydrocarbostyril and 5-Chloro-6 (4-hydroxypiperidino)- 3,4-dihydrocarbostyril were prepared from 6-(4-acetoxypiperidino)-3,4-dihydrocarbostyril in the same procedure as that described in Example 2, except using of N-chlorosuccinimide instead of N-bromosuccinimide.

7-Chloro-6-(4-hydroxypiperidino)-3,4-dihydrocarbostyril (Compound 5)

white powder
NMR (DMSO-$d_6$, 400 MHz)
δ: 1.60–1.75(2H, m), 1.90–2.05(2H, m), 2.52–2.56(2H, m), 2.75–3.00(2H, m), 3.15–3.30(2H, br), 3.65–3.80(1H, br), 7.02(1H, s), 7.22(1H, s), 10.05(1H, s)
mp 195°–199° C.

5-Chloro-6-(4-hydroxypiperidino)-3,4-dihydrocarbostyril (Compound 6)

white powder
NMR (DMSO-d6, 400 MHz)
δ: 1.50–1.59(2H, m), 1.82–1.84(2H, m), 2.43–2.46(2H, m), 2.61–2.67(2H, m), 2.95–2.98(2H, m), 3.02–3.07(2H, m), 3.57–3.62(1H, m), 4.63(1H, d, J=4.3 Hz), 6.77(1H, d, J=8.5 Hz), 6.98(1H, d, J=8.5 Hz), 10.06(1H, s)
mp 239°–243° C.

EXAMPLE 4

7-Cyano-6-(4-hydroxypiperidino)-3,4-dihydrocarbostyril (Compound 7)

To a solution of 100 mg of 7-bromo-6-(4-acetoxypiperidino) 3,4-dihydrocarbostyril in 1 ml of N,N-dimethylformamide was added 36 mg of copper(I) cyanide. After refluxing for 8 hr, an aqueous ethylenediamine and chloroform were added to the reaction mixture. The organic layer was washed with water, dried, evaporated under a reduced pressure, and the residue was purified by a silica gel column chromatography to obtain the nitril compound. 1N Sodium hydroxide (0.1 ml) was added to the solution of the nitrile compound in 1.5 ml of methanol. After stirring at room temperature for 1 hr, 0.1 ml of 1N hydrochloric acid and chloroform were added to the reaction mixture. The organic layer was washed with water dried and evaporated under a reduced pressure to give 30 mg of 7-cyano-6-(4-hydroxypiperidino)-3,4-dihydrocarbostyril.

white solid
NMR (DMSO-$d_6$, 270 MHz)

δ: 1.60–1.75(2H, m), 1.90–2.05(2H, m), 2.56(2H, dd, J=6.4 Hz, J=7.9 Hz), 2.90–3.00(2H, m), 3.03(2H, dd, J=7.1 Hz, 7.9 Hz), 3.35–3.45(2H, m), 3.74(1H, m), 4.81(1H, d, J=4.3 Hz), 7.16(1H, s), 7.19(1H, s), 10.22(1H, br-s)

mp 241°–246° C. (dec.)

EXAMPLE 5

6-(4-Hydroxypiperidino)-7-methoxycarbonyl-3,4-dihydrocarbostyril (Compound 8)

A solution of 30 mg of 7-cyano-6-(4-hydroxypiperidino)-3,4-dihydrocarbostyril in 3 ml of 2N sodium hydroxide was refluxed for 5 hr. 2N hydrochloric acid (3 ml) was added to the reaction mixture, and then the mixture was concentrated under a reduced pressure. The residue was dissolved in 2 ml of dichloromethane and 2 ml of methanol and a diazomethane-ether solution volume was added to the solution with stirring. Then, the solvent was evaporated under a reduced pressure, and the resulting residue was purified by a silica gel column chromatography to give 12 mg of 6-(4-hydroxypiperidino)-7-methoxycarbonyl-3,4-dihydrocarbostyril.

colorless needles
NMR (DMSO-$d_6$, 270 MHz)

δ: 1.45–1.60(2H, m), 1.75–1.85(2H, m), 2.42(2H, dd, J=7.2 Hz, J=7.8 Hz), 2.65–2.75(2H, m), 2.87(2H, dd, J=7.2 Hz, 8.1 Hz), 3.00–3.10(2H, m), 3.56(1H, m), 3.78(3H, s), 4.59(1H, d, J=4.3 Hz), 6.97(1H, s), 7.10(1H, s), 9.98(1H, br-s)

mp 157°–162° C.

EXAMPLE 6

6-(4-Hydroxypiperidino)-7-methyl-3,4-dihydrocarbostyril (Compound 9)

6-(4-Hydroxypiperidino)-7-methyl-3,4-dihydrocarbostyril was prepared from 5-(4-hydroxypiperidino)-2-nitro-p-tolaldehyde dimethylacetal in the same procedure as those described in Reference Examples 4 to 6.

white powder
NMR (DMSO-$d_6$, 400 MHz)

δ: 1.49–1.53(2H, m), 1.81–1.83(2H, m), 2.15(3H, s), 2.36–2.40(2H, m), 2.50–2.58(2H, m), 2.76–2.80(2H, m), 2.88–2.91(2H, m), 3.50–3.60(1H, br), 4.62(1H, d, J=3.9 Hz), 6.63(1H, s), 6.84(1H, s), 9.84(1H, s)

mp 159°–163° C.

EXAMPLE 7

7-Fluoro-6-(4-hydroxypiperidino) 3,4-dihydrocarbostyril (Compound 10)

7-Fluoro-6-(4-hydroxypiperidino)-3,4-dihydrocarbostyril was prepared from 4-fluoro-5-(4-hydroxypiperidino)- 2-nitrobenzaldehyde dimethylacetal in the same procedure as those described in Reference Examples 4 to 6.

white powder
NMR (DMSO-$d_6$, 400 MHz)

δ: 1.45–1.60(2H, m), 1.75 1.90(2H, m), 2.40(2H, t, J=7.5 Hz), 2.60–2.75(2H, m), 2.80(2H, t, J=7.5 Hz), 3.05–3.20(2H, m), 3.50–3.65(1H, m), 4.63(1H, d, J=4.1 Hz), 6.60(1H, d, J=13.1 Hz), 6.89(1H, d, J=9 0 Hz), 9.91(1H, s)

mp 214°–217° C.

EXAMPLE 8

6-(4-Propionyloxypiperidino)-7-nitro-3,4-dihydrocabostyril (Compound 11)

To a solution of 45 mg of 6-(4-hydroxypiperidino)-7-nitro-3,4-dihydrocabostyril in 1 ml of pyridine were added 40 mg of propionic anhydride and 4 mg of dimethylaminopyridine. After stirring at room temperature for 2 hr, the reaction mixture was concentrated under a reduced pressure. Water and chloroform were added to the residue. The organic layer was dried, evaporated under a reduced pressure, and the resulting residue was purified by a silica gel column chromatography to give 39 mg of 6-(4-propionyloxypiperidino)-7-nitro-3,4-dihydrocabostyril.

orange-colored powder
NMR (CDCl$_3$, 400 MHz)

δ: 1.16(3H, t, J=7.6 Hz), 1.81–1.89(2H, m), 2.00–2.06(2H, m), 2.35(2H, q, J=7.6 Hz), 2.64–2.67(2H, m), 2.90–3.02(4H, m), 3.14–3.20(2H, m), 4.92–4.98(1H, m), 7.01(1H, s), 7.28(1H, s), 8.31(1H, s)

mp 203°–210° C.

EXAMPLE 9

6-(4-Hydroxypiperidino)-7-trifluoromethyl-3,4-dihydrocarbostyril (Compound 12)

6-(4-Hydroxypiperidino)-7-trifluoromethyl-3,4-dihydrocarbostyril was prepared from ethyl 5-(4-hydroxypiperidino)-2-nitro-4-trifluoromethylcinnamate in the same procedure as that described in Reference Example 6.

pale yellow crystals
NMR (DMSO-$d_6$, 400 MHz)

δ: 1.46–1.54(2H, m), 1.79–1.81(2H, m), 2.44–2.51(2H, m), 2.73–2.79(2H, m), 2.92–2.95(2H, m), 3.03–3.08(2H, m), 3.58–3.63(1H, m), 4.63(1H, d, J=4.1 Hz), 7.22(1H, s), 7.29(1H, s), 10.13(1H, s)

mp 167°–169° C.

TEST EXAMPLE

Inhibitory Effect on Adenosine Diphosphate (ADP)-Induced Platelet Aggregation

Platelet rich plasma (PRP) was prepared from Japanese White rabbit blood drawn from the carotid artery into a syringe containing 3.8% sodium citrate (1/10) volume, and centrifuged at 400×g for 10 min. Platelet aggregation in PRP was induced by 20 μM ADP and determined by the turbidimetric method using an aggregomater (Hema-Tracer: Niko Bioscience Co., Ltd., Japan). The potency of the compound in this invention was expressed by the concentration at which the compound inhibited 50% of platelet aggregation (IC$_{50}$: μM).

| Compound | IC$_{50}$ μM | Compound | IC$_{50}$ μM |
|---|---|---|---|
| 1 | 37 | 7 | 18 |
| 2 | 55 | 8 | 42 |
| 3 | 26 | 9 | 130 |
| 4 | 140 | 10 | 51 |
| 5 | 26 | 11 | 37 |
| 6 | 290 | 12 | 39 |

What is claimed is

1. A piperidino-3,4-dihydrocarbostyril compound represented by the formula:

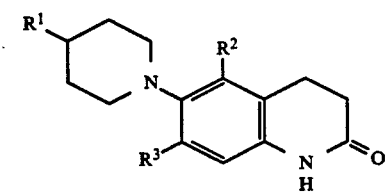

wherein $R^1$ represents a hydroxy group or an acyloxy group having 2 to 11 carbon atoms; one of $R^2$ and $R^3$ represents a nitro group, a cyano group, an alkoxycarbonyl group having 2 to 7 carbon atoms, an alkyl group having 1 to 4 carbon atoms, a haloalkyl group having 1 to 3 carbon atoms, or a halogen atom, and the other represents a hydrogen atom; and a pharmaceutically acceptable salt thereof.

2. A piperidino-3,4-dihydrocarbostyril compound as claimed in claim 1, represented by the formula:

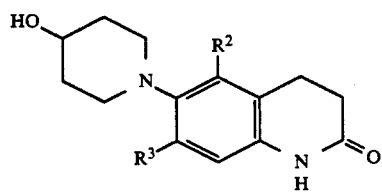

wherein one of $R^2$ and $R^3$ represents a nitro group, a cyano group, an alkoxycarbonyl group having 2 to 7 carbon atoms, an alkyl group having 1 to 4 carbon atoms, a haloalkyl group having 1 to 3 carbon atoms, or a halogen atom, and the other represents a hydrogen atom; and a pharmaceutically acceptable salt thereof.

3. A piperidino-3,4-dihydrocarbostyril compound as claimed in claim 2, represented by the formula:

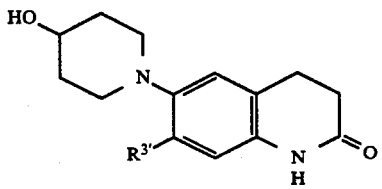

wherein $R^{3'}$ represents a nitro group, a cyano group, an alkoxycarbonyl group having 2 to 7 carbon atoms, an alkyl group having 1 to 4 carbon atoms, a haloalkyl group having 1 to 3 carbon atoms, or a halogen atom; and a pharmaceutically acceptable salt thereof.

4. A piperidino-3,4-dihydrocarbostyril compound as claimed in claim 3, represented by the formula:

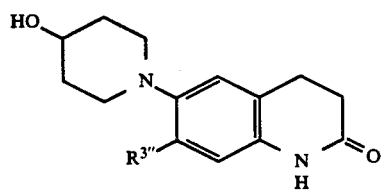

wherein $R^{3''}$ represents a cyano group, a haloalkyl group having 1 to 3 carbon atoms, or a halogen atom; and a pharmaceutically acceptable salt thereof.

5. The 7-fluoro-6-(4-hydroxypiperidino)-3,4-dihydrocarbostyril compound as claimed in claim 4, represented by the formula:

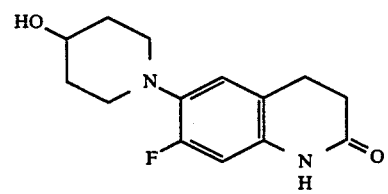

and pharmaceutically acceptable salts thereof.

* * * * *